US008556908B2

(12) United States Patent
Nycz et al.

(10) Patent No.: US 8,556,908 B2
(45) Date of Patent: Oct. 15, 2013

(54) OSTEOCHONDRAL IMPLANT PROCEDURE AND DEVICE

(75) Inventors: Jeffrey H. Nycz, Collierville, TN (US);
Keith M. Kinnane, Bartlett, TN (US);
Susan J. Drapeau, Cordova, TN (US);
Daniel Shimko, Germantown, TN (US);
Jeetendra Bharadwaj, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1384 days.

(21) Appl. No.: 11/680,318

(22) Filed: Feb. 28, 2007

(65) Prior Publication Data
US 2008/0208198 A1    Aug. 28, 2008

(51) Int. Cl.
*A61B 5/00* (2006.01)
*A61B 17/58* (2006.01)

(52) U.S. Cl.
USPC ............................................. 606/89; 606/87

(58) Field of Classification Search
USPC .............. 606/86 R–89, 96, 104; 33/511–512, 33/566; 623/23.72–23.76, 11.11, 14.12
See application file for complete search history.

(56) References Cited

U.S. PATENT DOCUMENTS

| | | | | |
|---|---|---|---|---|
| 5,100,409 A | * | 3/1992 | Coates et al. | 606/88 |
| 5,344,423 A | * | 9/1994 | Dietz et al. | 606/87 |
| 5,486,180 A | * | 1/1996 | Dietz et al. | 606/87 |
| 5,593,411 A | * | 1/1997 | Stalcup et al. | 606/88 |
| 6,554,838 B2 | * | 4/2003 | McGovern et al. | 606/87 |
| 7,160,307 B2 | * | 1/2007 | Harwood et al. | 606/89 |
| 2003/0051362 A1 | * | 3/2003 | Buckman et al. | 33/566 |
| 2003/0187458 A1 | * | 10/2003 | Carlson, II | 606/116 |
| 2004/0064193 A1 | * | 4/2004 | Evans et al. | 623/23.51 |

* cited by examiner

*Primary Examiner* — Matthew Lawson
(74) *Attorney, Agent, or Firm* — Sorell Lenna & Schmidt LLP

(57) ABSTRACT

A surgical procedure according to which a slotted film is positioned over an area of a bone to be milled; and a portion of a milling assembly is inserted in the defect, with another portion of the assembly extending through one of the slots so that the slot can be used as a guide to mill the bone.

15 Claims, 2 Drawing Sheets

OSTEOCHONDRAL IMPLANT PROCEDURE AND DEVICE

BACKGROUND

This invention relates to an improved osteochondral implant procedure and device, and more particularly, to such a procedure and device in which a recipient opening is prepared for receiving a graft.

In the human body, the knee consists of three bones—a femur, a tibia, and a patella—that are held in place by various ligaments. The corresponding chondral areas of the femur and the tibia form a hinge joint, and the patella protects the joint. Portions of the latter areas, as well as the underside of the patella, are covered with an articular cartilage, which allow the femur and the tibia to smoothly glide against each other without causing damage.

The articular cartilage often tears, usually due to traumatic injury (often seen in athletics) and degenerative processes (seen in older patients). This tearing does not heal well due to the lack of nerves, blood vessels and lymphatic systems; and the resultant knee pain, swelling and limited motion of the bone(s) must be addressed.

Damaged adult cartilages have historically been treated by a variety of surgical interventions including lavage, arthroscopic debridement, and repair stimulation, all of which provide less than optimum results.

Another known treatment involves removal and replacement of the damaged cartilage with a prosthetic device. However, the known artificial prostheses have largely been unsuccessful since they are deficient in the elastic, and therefore in the shock-absorbing, properties characteristic of the cartilage. Moreover, the known artificial devices have not proven able to withstand the forces inherent to routine knee joint function.

In an attempt to overcome the problems associated with the above techniques, osteochondral transplantation, also known as "mosaicplasty" has been used to repair articular cartilages. This procedure involves removing injured tissue from the damaged area and drilling openings in the underlying bone. One or more grafts, or plugs, consisting of healthy cartilage overlying bone, are obtained from another area of the patient, typically from a lower weight-bearing region of the joint under repair, or from a donor patient, and are implanted in the openings. In order to insure a precise fit between the graft and the opening, it is important that the opening is perpendicular to the plane of the bone. However, the curvature of the condyle of the femur makes this difficult.

An embodiment of the present invention involves a technique for insuring that the opening formed in the bone to receive the plug extends perperdicularly to the plane of the bone.

DETAILED DESCRIPTION

Figure 1:
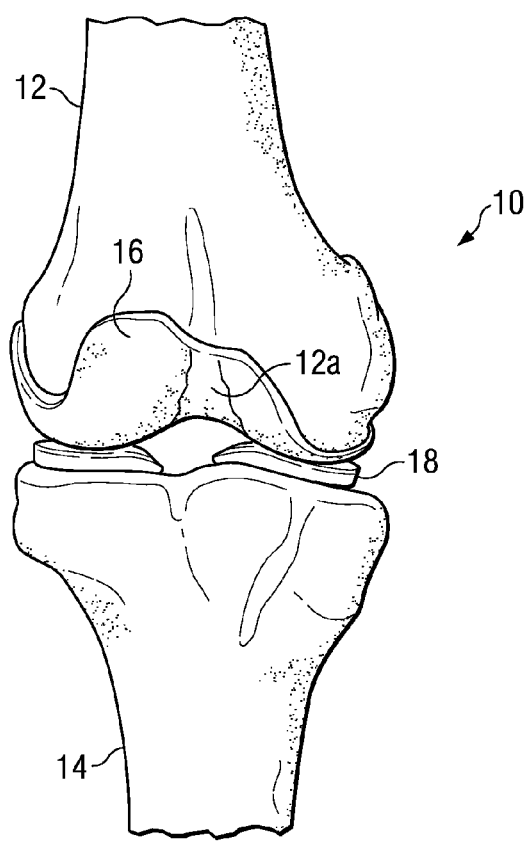
FIG. 1 is an elevational view of a human knee with certain parts removed in the interest of clarity.

Referring to FIG. 1, of the drawing, the reference numeral 10 refers, in general, to a knee area of a human including a femur 12 and a tibia 14 whose respective chondral areas are in close proximity. A cartilage 16 extends over a portion of the chondral area of the femur 12, and a meniscus 18 extends between the cartilage and the tibia 14. The patella, as well as the tendons, ligaments, and quadriceps that also form part of the knee, are not shown in the interest of clarity.

Figure 2:
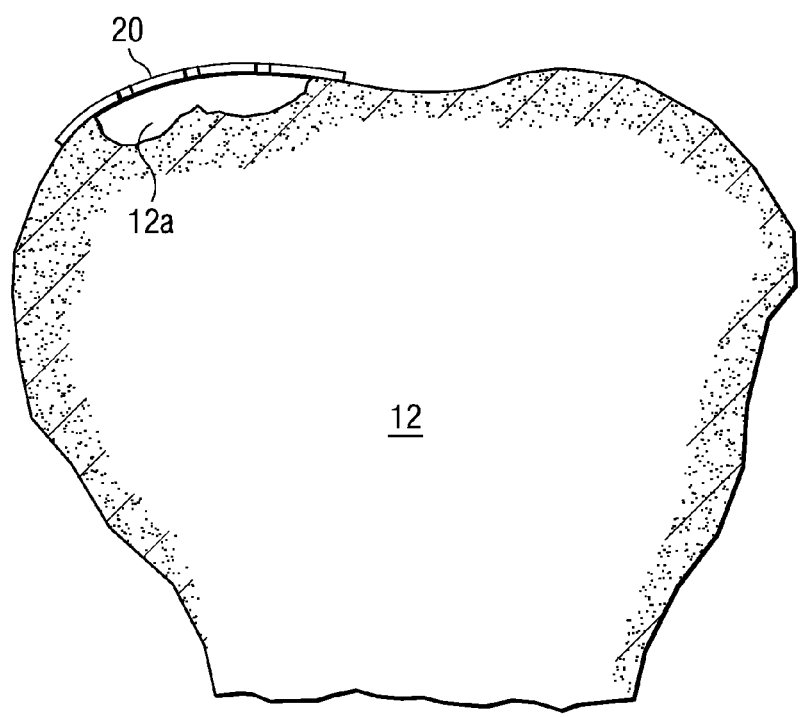
FIG. 2 is an enlarged, partial-sectional, partial-elevational view of the femur of the FIG. 1 with a film extending over a portion of the femur in accordance with an embodiment of the invention.

Referring to FIG. 2 which depicts the femur 12 of FIG. 1 in an inverted position, it will be assumed that a portion of the cartilage 16 extending over a chrondral area of the femur 12 has been damaged and removed by the surgeon, or has worn away, leaving a damaged area, or defect 12a. It will also be assumed that it is desired to use a milling tool, to be described, to mill out the bottom portion of the defect so that its curvature corresponds to the original curvature of the femur, before the defect occurred. Inasmuch as the surface of the femur surrounding the defect 12a is curved, this is a challenge.

Figure 3:
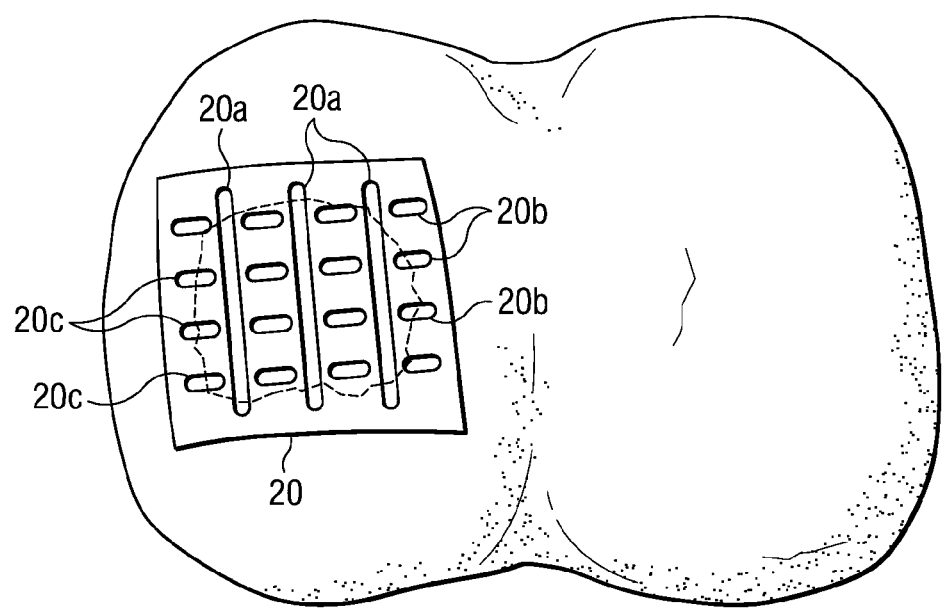
FIG. 3 is a top plan view of the femur and film of FIG. 2.

Referring to FIGS. 2 and 3, a film 20 is provided that is placed over the defect 12a and a portion of the femur 12 surrounding the defect. More particularly, the outer marginal portions of the film 20 extend over the surfaces of the femur 12 surrounding the defect, and the remaining portion of the film extends over the defect. The film 20 is secured to the latter surfaces in any conventional manner such as by adhesive, or the like. In this manner, since the outer, or upper, surface of the femur 12 is curved, that portion of the film extending over the defect 12a simulates the original curve of the femur before the defect was formed.

As shown in FIG. 3, that portion of the film 20 extending over the defect 12a has three relatively long, spaced, parallel through slots 20a, and four rows of relatively short, spaced parallel slots 22b extending in an alternating relationship with the slots 22a. Each row of slots 22b contains four spaced parallel slots extending perpendicular to the slots 20a.

Figure 4:
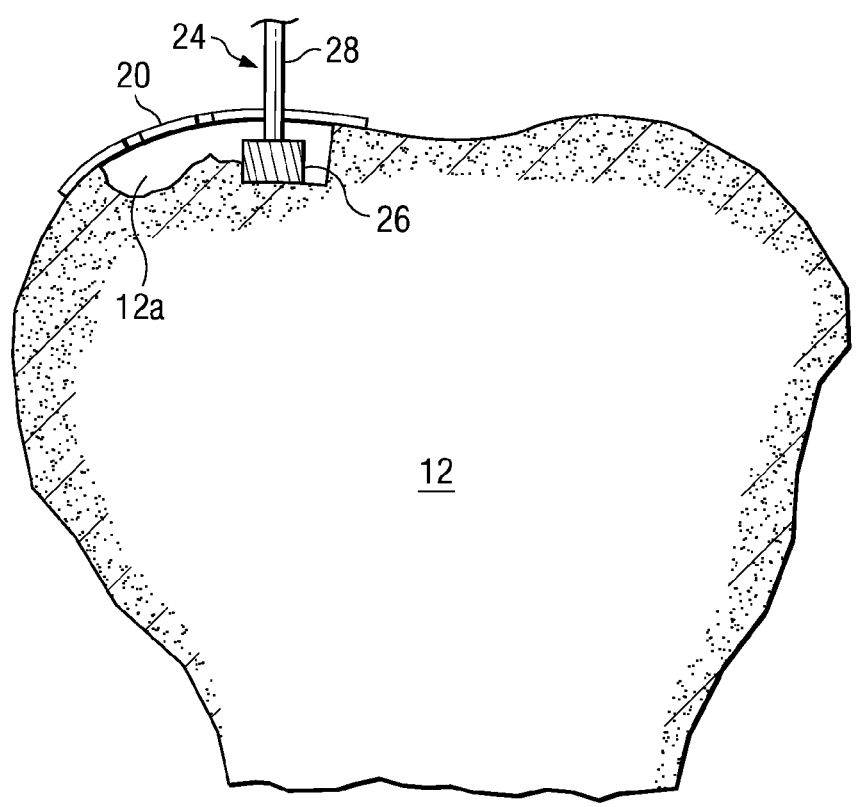
FIG. 4 is a view similar to that of FIG. 3, but depicting a milling tool extending through a slot in the film.

Referring to FIG. 4, a milling tool 24 is provided that includes a milling element 26 attached to, or formed integrally with, one end of a shank 28. The milling element 26 is shown extending in the defect 12 and underneath the film 20, and is cylindrical in cross section. The outer surface of the milling element 26 is treated in a conventional manner, such as by forming cutting elements, or the like, on the surface, so that, when the element is rotated at a relatively high speed, it mills portions of the femur 12 defining the defect.

It is understood that indicia, or graduations (not shown) can be applied to the outer surface of the shank for reasons to be described, and that the other end of the shank 28 is coupled to a electric drill, or similar device (not shown). The electric drill is adapted to receive the shank 28 in a chuck or similar device and, when activated, rotates the shank, and therefore the milling element 26 at a relative high rate of rotation.

Since, in the example illustrated in the drawing, the diameter of the milling element 26 (FIG. 4) is greater than that of the slots 20a and 20b (FIG. 3), a preferred technique would be to initially insert the shank from the bottom of the film 20 and through one of the slots 20a or 20b before the film is applied to the femur 12. Then the film 20, with the shank 28 extending through the latter slot, is applied to the femur 12 so that the milling element 26 rests on the bottom of the defect 12a, and a portion of the shank projects upwardly from the film as viewed in FIG. 4. The other end of the shank 28 is coupled to the electric drill.

The surgeon then cuts the bottom of the defect 12a, using the latter slot 20a or 20b as a guide for the shank 28, and therefore the milling element 26. More particularly, the surgeon can keep the shank 28 at a predetermined axial position relative to a slot 20a or 20b by aligning the film 20 with a graduation on the shank, as the bottom of the defect 12a is milled. In this manner, the milled portion will extend substantially parallel to the original surface of the femur 12 in which the defect 12a is formed. Alternately, a depth stop can be added to the shank 28 that has a diameter larger than the corresponding dimension of the slots 20a-20c. In use, the depth stop could rest on the film 20 to provide a consistent milling depth as the surgeon moves the tool 24 across the defect 12a. If the depth stop is used and the milling element 26 is smaller than the width or diameter of the slots 20a-20c, the film would not need to be moved to introduce the cutting tool into other slots on the film.

For the purpose of example, and referring to FIG. 4, the milling element 26 has been used to mill a portion of the bottom of the defect 12a (the portion to the right of the element as viewed in FIG. 4) so that the milled bottom portion extends substantially parallel to the original surface of the femur 12 in which the defect is formed.

When the surgeon has guided the shank 28 along the entire length of the slot (or that portion of the slot that is desired), the film 20, the shank 28, and the milling element 26 are removed from the vicinity of the defect 12a. The shank 28 is then inserted through another slot 20a or 20b and attached to the milling element 26 in the manner described above, and the procedure is repeated as needed using the latter slot as a guide in the manner described above.

After the bottom of the defect 12a has been adequately milled in accordance with the foregoing one or more implants can be implanted in the milled defect. The implants could be selected from the group consisting of an autograft, an allograft, a xenograft, a resorblable natural scaffold, a resorblable synthetic scaffold, a non-resorblable natural scaffold, a non-resorbable synthetic scaffold, a resorbable resurfacing implant and a non-resorbable resurfacing implant.

Therefore, when a graft is inserted in the defect 12a the cartilage portion of the graft is located in substantially the same position as the original damaged cartilage. Examples of procedures and apparatus for harvesting the grafts, forming the openings, and implanting the grafts are disclosed in U.S. application Ser. No. 11/340,024 filed on Jan. 26, 2006; U.S. application Ser. No. 11/338,926 filed on Jan. 25, 2006; U.S. application Ser. No. 11/339,194 filed on Jan. 25, 2006; U.S. Ser. No. 11/317,985 filed on Dec. 23, 2005; U.S. application Ser. No. 11/340,884 filed on Jan. 27, 2006; U.S. application Ser. No. 11/343,156 filed on Jan. 30, 2006; U.S. application Ser. No. 11/339,694; the disclosures of each of which are incorporated herein by reference.

Variations

1. The shape, dimensions, and type of the milling element can vary within the scope of the invention.
2. The number, size and locations of the slots in the film can vary.
3. After the milling is complete in accordance with the foregoing one or more additional tools can be used to shape the defect as needed, before the graft is implanted.
4. The spatial references mentioned above, such as "upper", "lower", "under", "over", "between", "outer", "inner" "above", and "surrounding" are for the purpose of illustration only and do not limit the specific orientation or location of the components described above.

Those skilled in the art will readily appreciate that many other variations and modifications of the embodiment described above can be made without materially departing from the novel teachings and advantages of this invention. Accordingly, all such variations and modifications are intended to be included within the scope of this invention as defined in the following claims. In the claims, means-plus-function clauses are intended to cover the structures described herein as performing the recited function and not only structural equivalents, but also equivalent structures.

What is claimed is:

1. A surgical procedure for milling a portion of a bone defining a defect, the procedure comprising:
    providing a slotted film comprising a plurality of slots positioned within a periphery of the slotted film and entirely enclosed therein, each of said slots having a first width, said slotted film having a back surface and an opposite front surface;
    providing a milling tool comprising a shank having a second width and a milling element having a third width engaged with said shank, the second width being less than the first width and the third width being greater than the first width;
    inserting said shank from said back surface into one of said slots of said slotted film;
    positioning said slotted film over an area of the bone to be milled after said shank is inserted into said one of said slots such that said back surface of said slotted film engages
said bone and said milling element is positioned within the defect;
    using said one of said slots as a guide to mill the bone;
    milling the bone;
    removing said shank from said one of said slots; and
    inserting said shank from said back surface into a second of one of the slots.

2. The procedure of claim 1 further comprising guiding an axial position of the tool using at least one of the slots so that the tool mills a bottom of the defect in a manner so that the milled bottom of the defect extends substantially parallel to the original surface of the bone in which the defect is formed.

3. The procedure of claim 2 further comprising using a depth gauge on the tool that cooperates with at least one of the slots to guide the milling of the bone.

4. The procedure of claim 3 further comprising harvesting at least one graft from another area of a patient/recipient, or from a corresponding area of a donor.

5. The procedure of claim 1 further comprising guiding an axial position of the tool using at least one of the slots so that the tool mills a bottom of the defect in a manner so that a curvature of the milled bottom of the defect corresponds to an original curvature of a femur bone of a patient, before the defect occurred.

6. The procedure of claim 5 further comprising wherein the step of milling comprises milling at least one opening in the bottom, and implanting a graft in each opening.

7. The procedure of claim 1 wherein the milled bone forms an opening and further comprising filling the opening with an implant selected from the group consisting of an autograft, an allograft, and a xenograft.

8. The procedure of claim 1 wherein the milled bone forms an opening and further comprising filling the opening with an implant selected from the group consisting of a resorblable natural scaffold, a resorblable synthetic scaffold, a non-resorblable natural scaffold and a non-resorbable synthetic scaffold.

9. The procedure of claim 1 wherein the milled bone forms an opening and further comprising filling the opening with an implant selected from the group consisting of a resorbable resurfacing implant and a non-resorbable resurfacing implant.

10. The procedure of claim 1 wherein the bone is a femur and wherein the defect is an opening in the femur.

11. The procedure of claim 10 wherein an upper surface of the femur is curved, and wherein a portion of the film extending over the defect simulates an original curve of the femur before the defect was formed.

12. The procedure of claim 1 wherein said plurality of slots comprises a plurality of spaced apart first slots extending parallel to one another and a plurality of rows of second slots, each of said second slots extending perpendicular to said first slots.

13. The procedure of claim 12 wherein at least some of said second slots are positioned between said first slots.

14. The procedure of claim 12 wherein each of said second slots are positioned in an alternating relationship with said first slots.

15. The procedure of claim 1 wherein said plurality of slots comprises three spaced apart first slots extending parallel to one another and four rows of second slots, each of said second slots extending perpendicular to said first slots, said second slots being positioned in an alternating relationship with said first slots.

\* \* \* \* \*